United States Patent [19]

Ishikawa

[11] Patent Number: 4,533,222
[45] Date of Patent: Aug. 6, 1985

[54] EYE EXAMINING INSTRUMENT
[75] Inventor: Yasuyuki Ishikawa, Kawaguchi, Japan
[73] Assignee: Canon Kabushiki Kaisha, Tokyo, Japan
[21] Appl. No.: 632,680
[22] Filed: Jul. 20, 1984

Related U.S. Application Data

[63] Continuation of Ser. No. 521,015, Aug. 8, 1983, abandoned, which is a continuation of Ser. No. 197,593, Oct. 16, 1980, abandoned.

[30] Foreign Application Priority Data
Oct. 25, 1979 [JP] Japan .................. 54-137944

[51] Int. Cl.³ .............. A61B 3/14; A61B 3/10
[52] U.S. Cl. .................. 351/206; 351/211; 351/237; 350/276 SL
[58] Field of Search ........... 351/222, 237, 243, 244, 351/245; 350/580, 276 SL, 291, 601

[56] References Cited

U.S. PATENT DOCUMENTS

| | | | |
|---|---|---|---|
| 1,879,216 | 9/1932 | Hannan et al. | 351/44 |
| 2,081,969 | 6/1937 | Allen et al. | 351/13 |
| 2,619,872 | 12/1952 | Shepard | 351/37 |
| 2,649,839 | 8/1953 | Condon | 350/58 |
| 2,711,667 | 6/1955 | Simjian | 350/291 |
| 3,586,424 | 6/1972 | Schenk | 351/14 |
| 4,293,198 | 10/1981 | Kohayakawa et al. | 351/14 |
| 4,372,655 | 2/1983 | Matsumura et al. | 351/206 |

FOREIGN PATENT DOCUMENTS 547216  5/1956  Belgium ................. 351/44

OTHER PUBLICATIONS

Cooper et al., *Nikon F, Nikkormat Handbook of Photography,* American Photographic Book Publishing Co., Inc. New York, © 1968 pp. (2-1)-(2-6), (12-11)-(12-12).

*Primary Examiner*—R. A. Rosenberger
*Attorney, Agent, or Firm*—Fitzpatrick, Cella, Harper & Scinto

[57] ABSTRACT

An eye examining instrument comprises examining means disposed to project an examining light to and receive the light from the eye of a person to be examined; a casing for encasing said examining means; a beam splitter disposed on the outside of said casing for directing the examining light to the eye to be examined, said beam splitter having sufficient width to allow both eyes of the person to be examined to see a fixation object and being directly opposed to the eye to be examined; and a cover connected with said casing for preventing any undesirable light from coming into said beam splitter.

13 Claims, 6 Drawing Figures

EYE EXAMINING INSTRUMENT

This application is a continuation of application Ser. No. 521,015, filed Aug. 8, 1983, now abandoned, which was a continuation of application Ser. No. 197,593, filed Oct. 16, 1980, now abandoned.

BACKGROUND OF THE INVENTION

1. Field of the Invention

The present invention relates to an ophthalmological examining instrument and more particularly to such an instrument for examining an eye with mitigates measuring errors otherwise caused by externally scattered light such as room lamp.

2. Description of the Prior Art

For examining a human eye it is a common practice in the art to fix the eye of a person to be examined on a certain fixation object. For example, in case of an eye refractometer, a target image is optically formed in a light-shielded casing containing the functional part for measuring. The eye of a person to be examined is fixed upon the formed target image. However, it is known that this examining method has a problem. When the apparent distance from the eye to the target image is set to five meters or less, the person in practice is apt to assume a posture forwardly looking into the target image. This results in a state similar to short sightedness which is generally called as mechanical myopial. Due to the unfavourable pheonomenon, the measured eye refractive power is different from the actual refractive power of the same eye in ordinary use. For this reason it is undesirable to interpose any converging or diverging optic between a person to be examined and a fixation object in conducting an examination for myopia.

For some kinds of eye examining instruments the person to be examined is required to fix his one eye to be examined upon a target image while covering the other eye with a hand or the like. However, as is known in the art, there is some difference in refractive power conditioning between sight by two eyes and sight by a single eye. In view of this point it is preferred that the eye examination be conducted under a natural condition, that is, under the condition of sight by two eyes.

Also, it is well known that the result of an eye examination is affected by the illuminance of an image or object upon which the eye is to be fixed as well as the illuminance of the surroundings about the person to be examined. The result obtained by examining an eye in a dark room or with the eye being fixed upon an object placed in the dark is sometimes different from the result obtained by examining the same eye under ordinary brightness. For this reason it is undesirable that eye examination be conducted while the face of a person to be examined is put against a light-shielded tube of the examining instrument.

As seen from the above, when a person is compelled to look at an object under unusual conditions for conducting an eye examination, his eyes exhibit a different response from that exhibited under usual conditions. Therefore, it is desirable that an eye examination be conducted under a condition as similar to that in daily life as possible. Furthermore, many eye doctors agree that examination or measurement of a human eye should be conducted while observing the expression on the face of one whose eye is being examined or measured. They say that accuracy of the examination or measurement can be improved by doing so and this is particularly true for subjective eye examination or measurement.

In our prior application, Japanese Patent Application No. 115,647/1978 (U.S. Ser. No. 75,115, now U.S. Pat. No. 4,372,655) there is disclosed an embodiment for conducting an eye examination under the conditions with both eyes seeing and ordinary illumination. While the embodiment of the prior invention has satisfied the above requirements for eye examination, it was characterized by another problem. According to the embodiment, a beam splitter is interposed between the eye to be examined and the fixation object. A scene of the examining room is projected on a splitting surface of the beam splitter by which the examined person's attention is distracted. In addition, since the person looks at the projected scene, the direction and sight of the eye is affected by it. This is the problem involved in the embodiment of the prior invention. A similar problem may arise even when an optical and electrical filter system is provided in the measuring part. In this case, it is desired to prevent external light such as room light from entering the objective system.

SUMMARY OF THE INVENTION

Accordingly, it is an object of the present invention to prevent adverse effects of undesirable light on eye examination.

It is another object of the invention to provide an eye examining instrument which allows the examined person to look at the fixation object with both eyes.

It is a further object of the invention to provide an eye examining instrument which permits measurment of eye refractive power without need of interposition of an optic having power in the optical path between the eye to be examined and the fixation object.

It is still a further object of the invention to make it possible to examine and measure a human eye without need of a dark room.

Other and further objects, features and advantages of the invention will appear more fully from the following description taken in connection with the accompanying drawings.

As automatic eye refractometer there may be used the apparatus proposed by our prior application, Japanese Patent Application laid open No. 52,893/1979 (U.S. Ser No. 944,304, now U.S. Pat. No. 4,293,198, issued Oct. 6, 1981) and other various known apparatus in carrying out the present invention. In the following description, preferred embodiments of the present invention will be described with reference to the embodiment of the aforementioned prior application.

DESCRIPTION OF PERFERRED EMBODIMENTS

Figure 1:
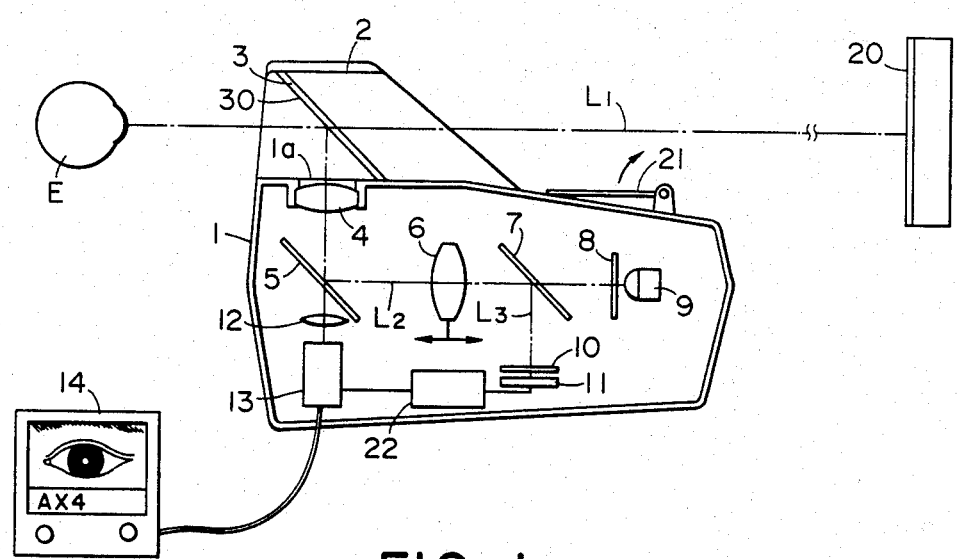
FIG. 1 is a shematic sectional view of an embodiment of the invention.
Figure 2:
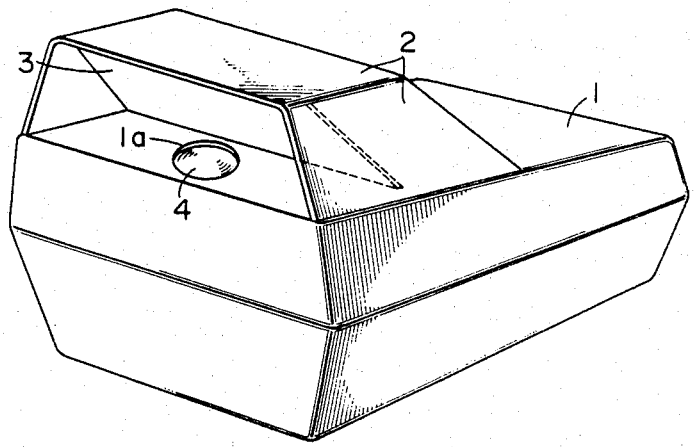
FIG. 2 is a perspective view thereof.

In FIG. 1 reference character E designates an eye to be examined, 1 is a casing containing the functional part of the eye examining instrument and 1a is an opening provided in the casing. 2 is a light shielding cover connected with the casing 1. The cover 2 is so shaped as to cover the upper side and both lateral sides of a beam splitter 3 as seen best in FIG. 2. The cover 2 shields the beam splitter 3 and the opening 1a of the casing from light coming from one or more room lamps (not shown).

The beam splitter 2 may be, for example, a known wavelength splitting mirror which reflects infrared light and transmits visible light. The beam splitter 2 has sufficient width to allow the person to be examined to look at a fixation object with both eyes at the same time. To examine both eyes, the examining instrument is shifted leftward and rightward relative to the examined person and examination is conducted one eye after the other eye. Therefore, the width of the beam splitter is measured so as to sufficiently cover the view field by both eyes in any case even when the instrument is moved leftward and rightward. However, if the beam splitter is designed in such manner that it can be moved simultaneously with the movement of the instrument, it is unnecessary for the beam splitter to have so large width. A width about two times larger than the distance between two eyes of a person is sufficient for this purpose.

Figure 6:
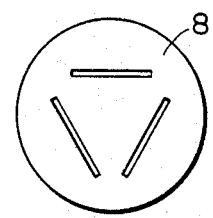
FIG. 6 is a plan view of one component thereof.

Designated by 4 is an objective lens which is disposed behind the opening 1a with its optical axis extenting vertically. 5 is a mirror whose ratio of reflection to transmission is about 4:1. 6 is a moving lens which is moved on and along the optical axis $L_2$ by carrying means not shown. 7 is a half mirror and 8 is a mask. As illustrated in FIG. 6, the mask has linear slits formed therein extending normal to three meridians respectively. 9 is an infrared light source for illuminating the mask. 10 is a second mask in which linear slits normal to the three meridians are formed in the same manner as in the first mask 8. 11 is a photo detector having three photo receiving areas behind the three slits of the mask 10 respectively. The three photo receiving areas function independently of each other.

The two masks 8 and 10 are disposed normal to the optical axes $L_2$ and $L_3$ respectively and also conjugated relative to the half mirror 7. Designated by 12 is a relay lens, 13 is a video camera provided with an image pick-up tube such as silicon vidicon and 14 is a television monitor on which appears a front image of the anterior part of the eye being examined. Although not shown in the drawings, the casing 1 is supported by a supporting mechanism. The supporting mechanism includes supporting posts for adjustment of the casing position in the vertical direction and a handle for moving the casing horizontally including forward, backward, leftward and rightward. In addition, the supporting mechanism includes a face fixing pad on which the face of the person to be examined is fixed.

Designated by 20 is a fixation object which is disposed on the optical axis $L_1$ of the examined eye E and spaced from the examined eye by a suitable distance which may be, for example, 5 m (five meters). 21 is a fixation object for short distance examination. When used, the fixation object 21 is turned up to its upright position as suggested by arrow. 22 is an electronic circuit comprising an output processing circuit, a computing circuit and a video character signal generating circuit. An example of the video character signal generating circuit included in the electronic circuit 22 is disclosed in U.S. Pat. No. 3,345,458 (Japanese Patent Publication No. 38,925/1971). Through the electronic circuit 22 the result of computing by the computing circuit can be displayed on the television receiver 14 together with an image of the examined eye in the form of character and numeral on a white background as illustrated in FIG. 1.

The manner of operation of the above described embodiment is as follows:

At first, the operator turns the light source 9 on and drives the image pick-up tube 13 and television receiver 14. Then, a person to be examined is guided to the face fixing pad not shown. After fixing his face on the fixing pad and approximately aligning the one of his eye to be examined with the opening 1a, the operator or the examiner makes him looking at the fixation object 20 through the beam splitter 3. During the time, an image of the anterior part of the eye appears on the television receiver 14. The operator moves the casing 1 vertically and horizontally for adjustment while watching the image on the television receiver 14. The adjustment is finished when the image on the television screen has become sharp and clear and the center of the anterior part, in particular, of the pupil of the eye to be examined has been aligned with the center of the television picture plane. After the completion of adjustment, an examination of the eye can be started.

Infrared light emitted from the light source illuminates the mask 8 having three slits. The infrared light emerging from the individual slits in the mask 8 passes through the splitting mirror and enters the moving lens 6. After being converged by the lens 6, the infrared light is reflected by the mirror 5 and then once focused. Thereafter, the infrared light enters the objective lens 4 which converges the light once more. The converged light is reflected by the reflecting surface 3a of the beam splitter toward the eye E. The light made incident on the eye E forms an image of the slits on the fundus of the eye or in the vicinity of the fundus.

A beam of light reflected upon the fundus emerges from the eye E and then it is reflected toward the objective lens 4 by the beam splitter 3. After being focused by the objective lens 4, the beam is reflected by the mirror 5 toward the moving lens 6 which converges the beam. The beam is again reflected by the mirror 7 and directed to the mask 10 on which the beam is focused.

The image of the slits formed on the mask is sharp and clear when the masks 8 and 10 are conjugated with the eye fundus relative to the relay optical system. However, the slit image is more or less blurred before and after the point of the conjugation. Accordingly, the quantity of light passed through the mask 10 is decreased and therefore the output of the photo detector 11 becomes smaller than that obtained at the conjugated point. To detect this change of the quantity of light passed through the mask, the light is continuously measured photometrically while moving the moving lens 6 to shift the position of the slit image projected on the fundus in the direction of the optical axis. The position of the moving lens 6 in which the photometric value becomes maximum will give information of refractive power of the examined eye E. Therefore, the refractive power in a given meridional direction can be calculated from the data, namely, from the position of the moving lens 6.

During the above measurement, the person to be examined continues looking at the fixation object 20 through the beam splitter 3. The beam splitter 3 is formed of a glass plate. The inside surface 3a of the glass plate facing the subject person has a multilayer interferential film applied thereon by a vapour deposition technique. The other surface, namely, the outside surface of the glass plate is treated with reflection reducing optical coating. The glass plate treated in this manner has a high visible light transmissivity reaching about 98%. However, it still reflects the light of the room lamp in the examining room at a rate of about 2%. Since an image of the reflected light is visible to the person to be examined, it disturbs the person in looking at the fixation object and the fixing of his eye is made unstable thereby. This is a problem to be solved by the present invention.

As previously described, an image of the anterior part of the examined eye is focused on the image pick-up surface of the pick-up tube 13 through the objective lens 4 and relay lens 12 and the image is displayed on TV monitor 14. In this case, if any intense light such as that from the ceiling light in the examining room enters the objective lens, then the image of the anterior eye part is degraded very much. This constitutes another problem.

To solve the above problems according to the invention, a screen or shielding member 2 is provided for the beam splitter and objective lens. The screen member 2 covers the beam splitter and objective lens so as to shield them from undesirable light while providing a sufficiently large space in front of the examined eye to provide the full view field for both eyes of the examined person. Thus, provision of such shielding member 2 permits an eye examination to be conducted in a room illuminated as usual. The examined person can look at the fixation object in a nearly natural state and the examiner can observe a sharp and clear image of the examined eye on the screen of TV monitor. The shielding member 2 serves also to prevent the examined person from accidentally contacting with the beam splitter which may injure the person or result in breaking of the beam splitter. In addition, the shielding member protects the beam splitter 3 from dust.

The shielding member 2 is preferably so formed as to be removable from the casing easily for the purpose of cleaning of the beam splitter 3 or the like. An concrete form of such detachable shielding member is shown in FIGS. 3 and 4.

Figure 3:
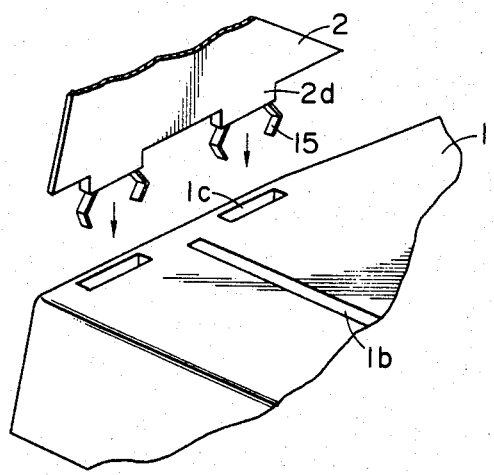
FIG. 3 is a perspective view of the essential part of the embodiment.
Figure 4:
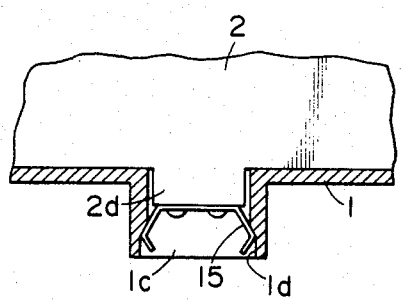
FIG. 4 is a sectional view thereof.

In FIG. 3, reference numeral 1b designates a slot for mounting the beam splitter 3. The shielding member 2 has lower projections 2d. A pair of springs 15 are fixed to the bottom end of each projection 2d. Each projection 2d with springs 15 is inserted into a slot 1c provided on the casing. As shown in FIG. 4, each the slot 1c has a pair of notches 1d. When the shielding member 2 is inserted into the slots 1c to the position shown in FIG. 4, the springs 15 come into engagement with the notches 1d so that the shielding member can be held in the position steadily. If the shape of the projection 2d including that of the springs 15 is moulded using resin, then the springs 15 may be omitted because of the elasticity of the resin.

Figure 5:
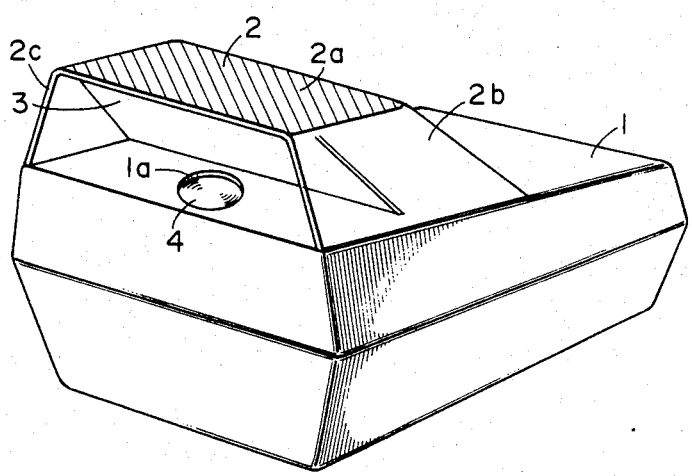
FIG. 5 is a perspective view of another embodiment of the invention.

FIG. 5 shows another form of the shielding member 2.

In this embodiment, the shielding member 2 has a particular ceiling part 2a made of such material which does not transmit visible light, infrared light or ultraviolet light. Instead of making the ceiling part from such material, a coating layer of such material may be applied on the ceiling part 2a. The side surfaces 2b and 2c are formed of light transmissive plate having a multilayer interferential film applied thereon by a vapour deposition technique. The multilayer film transmits visible light but does not transmit examining light such as infrared light. With the structure of the shielding member shown, the examiner can observe the expression on the face of the person to be examined very well during eye examination and undesirable light can be shut out effectively.

When eye examination is conducted with the apparatus according to the invention, the examiner should take care than any unnecessary object does not enter the area between the examined eye and the fixation object. This is essential for attaining a stable fixation of the examined eye. The examiner should not stand in such position in which his face or head enters the view field of the examined eye looking at the fixation object. In this sense, it is preferred that the examiner positions himself to one side of the examining apparatus during examination. With the shielding member having transparent side surfaces, the examiner can observe the expression of the examined eye very well while standing at such position.

As well understood from the foregoing, the present invention brings forth many advantages over the prior art. According to the invention, eye examination can be conducted within a room having an ordinary brightness and of a person who is looking at the fixation object with both eyes in a natural state. Also, the examiner can observe the examined person very well during examination.

What I claim is:

1. An eye examining instrument comprising:
   examining means, for measuring a refraction error of each eye of a person to be examined, said examining means projecting an invisible examining light to be directed to the examined eye and receiving the invisible examining light reflected from the examined eye;
   a casing containing said examining means formed with an opening that opens upwardly through which the invisible examining light is projected to be directed to the examined eye and through which the invisible examining light is received from the examined eye;
   beam splitting means disposed on the outside of said casing for directing said invisible examining light to the examined eye and permitting the person being examined to view a fixation object spaced from said casing, said beam splitting means including a mirror that transmits visible light and reflects the invisible examining light, said mirror having a sufficient width to allow both eyes of the person to be examined to view simultaneously the fixation object while either of the person's eyes can be examined by moving said instrument laterally with respect to the eyes; and
   shielding means for covering said beam splitting means so as to shield it from undesirable light but for allowing the eye to view the fixation object through said beam splitting means, said shielding means having a top surface and two side surfaces, said side surfaces transmitting visible light, and said top surface being opaque.

2. An eye examining instrument according to claim 1 wherein said side surfaces are spaced by a distance sufficient so that said side surfaces do not interfere with the field of view of the fixation object of both eyes of a person to be examined.

3. An eye examining instrument according to claim 1, wherein said mirror is disposed directly opposed to the examined person.

4. An eye examining instrument according to claim 1, wherein said mirror has a multilayer interferential film applied onto its parallel plane plate.

5. An eye examining instrument according to claim 1, which further comprises a second fixation object supported on said casing for fixing the examined eye.

6. An eye examining instrument according to claim 1, wherein said examining means includes a video camera, sensitive to visible light, for taking an image, through said opening, of an interior of the eye to be examined.

7. An eye examining instrument according to claim 1, wherein said examining means includes an objective lens disposed in said opening and having a vertically extending optical axis.

8. An eye examining instrument comprising:

examining means, for measuring a refraction error of each eye of a person to be examined, said examining means projecting an invisible examining light to be directed to the examined eye and receiving the invisible examining light reflected from the examined eye;

a casing containing said examining means formed with an opening that opens upwardly through which the invisible examining light is projected to be directed to the examined eye and through which the invisible examining light is received from the examined eye;

beam splitting means disposed on the outside of said casing for directing said invisible examining light to the examined eye and permitting the person being examined to view a fixation object spaced from said casing, said beam splitting means transmitting visible light and reflecting the invisible examining light; and shielding means for covering said beam splitting means so as to shield it from undesirable light but for allowing the eye to view a fixation object through said beam splitting means, said shielding means having a top surface and two side surfaces, said side surfaces transmitting visible light, and said top surface being opaque.

9. An eye examining instrument according to claim 8, wherein said beam splitting means comprises a mirror and is disposed directly opposed to the examined person.

10. An eye examining instrument according to claim 9, wherein said mirror has a muitilayer interferential film applied onto its parallel plane plate.

11. An eye examining instrument according to claim 8, which further comprises a second fixation object supported on said casing for fixing the examined eye.

12. An eye examining instrument according to claim 8, wherein said examining means includes a video camera, sensitive to visible light, for taking an image, through said opening, of an interior of the eye to be examined.

13. An eye examining instrument according to claim 8, wherein said examining means includes an objective lens disposed in said opening and having a vertically extending optical axis.

* * * * *